(12) United States Patent
Rosner

(10) Patent No.: US 6,387,361 B1
(45) Date of Patent: May 14, 2002

(54) USE FOR DRUG ACARBOSE PRECOSE FOR WEIGHT CONTROL PREVENTION OF WEIGHT GAIN FOR WEIGHT LOSS FOR TREATMENT AND PREVENTION OF OBESITY

(76) Inventor: Harvey Rosner, 530F Grand St. Apt. 3F, New York, NY (US) 10002

(*) Notice: Subject to any disclaimer, the term of this patent is extended or adjusted under 35 U.S.C. 154(b) by 0 days.

(21) Appl. No.: 09/364,992

(22) Filed: Aug. 2, 1999

(51) Int. Cl.$^7$ ................................................ A61K 31/74
(52) U.S. Cl. ...................................... 424/78.01; 435/18
(58) Field of Search ........................... 424/78.01; 435/18

(56) References Cited

U.S. PATENT DOCUMENTS

| | | | |
|---|---|---|---|
| 4,062,950 A | * 12/1977 | Frommer et al. | |
| 5,322,697 A | * 6/1994 | Meyer | 424/458 |
| 5,753,253 A | * 5/1998 | Meyer | 424/439 |

OTHER PUBLICATIONS

Shibata Et Al., vol. 189, pp. 309–322 (1989).*
Brunton Et Al., The American Academy of Family Physicians, pp. 1–16, (1996).*

* cited by examiner

Primary Examiner—James O. Wilson

(57) ABSTRACT

Control of weight gain has long been a problem for many people who if they lose weight by dieting often gain it back in a short period of time. Therefore, there has been much research to find a simple means to control weight in humans.

Acarbose, an oligosaccharide, is an oral alpha glucosidase inhibitor. The mechanism of action of acarbose results from a competitive inhibition of pancreatic amylase and membrane bound intestinal aplpha-glucoside hydrolase enzymes. Pancreatic alpha amylase hydrolizes complex starches in the lumen of the small intestine. The membrane bound intestinal alpha glucosidases hydrolyze oligo saccharides, trissaccharides and disaccharides to glucose and other monosaccharides in the brush boarder of the small intestines. It has no inhibitory effect against lactase and would therefore not be expected to induce the symptoms of lactose intolerance. The weight gain or loss for an individual is essentially the difference between the calories absorbed and the calories burned.

4 Claims, No Drawings

USE FOR DRUG ACARBOSE PRECOSE FOR WEIGHT CONTROL PREVENTION OF WEIGHT GAIN FOR WEIGHT LOSS FOR TREATMENT AND PREVENTION OF OBESITY

OBJECTS OF THE INVENTION

It is an object of the invention to control weight in humans by ingesting acarbose with meals with food containing carbohydrates.

This and other objects and advantages will become obvious from the following detailed description.

THE INVENTION

The invention is directed to a method of controlling weight in human beings by ingesting acarbose at meals with food containing carbohydrates. Acarbose is known to be an oral -glucosidase inhibitor, which acts by a reversible inhibitor of membrane-bound intestinal -glucoside hydraslase enzymes. Membrane intestinal -glucosidases hydrolize oligosaccharides and disaccharides to glucose and other monosaccharides in the brush border of the small intestine.

Weight gain or loss for an individual is essentially the difference between the amount of calories absorbed and the amount of calories burned. Acarbose apparently exerts it's effect by blocking the absorption of carbohydrates, which means a portion of the carbohydrates consumed at the meal are not absorbed by the body but are excreted by the body rather than absorbed due to the action of acarbose. Acarbose does not affect the digestion of proteins or fats. This lower absorption of carbohydrates results in less weight gain due to the lower consumption of calories.

To be effective, the diet must contain carbohydrates above the monosacchoride level and the use of acarbose for weight control is a major breakthrough in the field of weight control. Treatment with acarbose is a relatively safe method for weight control as the side effects of acarbose are minimal as can be seen from the 2000 physician's desk manual.

Acarbose has been used for the treatment of type II diabetes and is marketed under the mark Precose® by Bayer in tablet dose of 25, 50 and 100 mg. Acarbose is a prescription drug and the exact dosage for weight control will be determined by the attending physician as a result of the clinical response of the patient. I have determined from my studies that normally the dosage per meal is dependent upon the amount of carbohydrates in the meal. Acarbose can also be administered as a wafer or can be mixed with the food to reduce the carbohydrate absorption.

The method of weight control can be used to control weight gain, to provide weight loss and for the prevention or treatment of obesity depending upon the amount of carbohydrates consumed at the meals. For example, if a person overindulge during the holiday season, the consumption of acarbose at the meals will lower the amount of weight gained because at least a portion of the carbohydrates are excreted rather than absorbed.

Besides blocking absorption of carbohydrates, acarbose encourages bacterial fermentation in the digestive tract for more gas production, which gives the feeling of fullness, reducing the amount of food consumed at the meal. This results in a psychological deterrent to over eating.

Various modifications of the method of the invention may be made without departing from the spirit or scope thereof. It is to be understood that the invention is intended to be limited only as defined in the appended claims.

What I claim is:

1. A method of controlling weight in a human comprising administering to humans in need thereof with a meal of carbohydrate containing food an amount of acarbose sufficient to lower carbohydrate absorption.

2. The method of claim 1 wherein the human is obese.

3. The method of claim 1 wherein the amount of acarbose used results in a weight loss by the human.

4. The method of claim 1 wherein the amount of acarbose used results in reduced weight gain.

\* \* \* \* \*